US00PP27954P2

(12) United States Plant Patent
Warren

(10) Patent No.: US PP27,954 P2
(45) Date of Patent: May 2, 2017

(54) CRABAPPLE TREE NAMED 'JFS-KW207'

(50) Latin Name: *Malus*
Varietal Denomination: JFS-KW207

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 14/757,327

(22) Filed: Dec. 16, 2015

(51) Int. Cl.
*A01H 5/00* (2006.01)

(52) U.S. Cl.
USPC ..... Plt./173

(58) Field of Classification Search
USPC ..... Plt./173
See application file for complete search history.

*Primary Examiner* — Annette Para
(74) *Attorney, Agent, or Firm* — Klarquist Sparkman, LLP

(57) ABSTRACT

A variety of crabapple which combines compact growth, dense foliage, dwarf habit, pinkish white flowers and brightly colored ornamental fruit with excellent resistance to fireblight and apple scab.

11 Drawing Sheets

Latin name of the genus and species of the plant claimed: *Malus*.

Variety denomination: 'JFS-KW207'.

BACKGROUND OF THE INVENTION

In the fall of 1992, I collected fruit from a large collection of crabapple cultivars and open pollinated crabapple seedlings growing in Boring, Oreg. From these, I extracted seed and sowed the seed in beds in a Boring, Oreg. nursery. From this bed, I obtained 918 seedlings that I planted into a testing row for evaluation and possible cultivar selection. In the fall of 1996, I selected a compact dwarf crabapple tree which I named 'KW-8MX' (unpatented). I evaluated its potential over the next several years. While promising, I decided that 'KW-8MX' did not have all of the qualities that I desired in a new cultivar, especially in that its flowers were somewhat small and poorly shaped.

As *Malus* 'KW-8MX' did possess an unusually dwarf and compact habit, I decided to pursue cultivar improvement by growing large populations of its seedlings for selection. In the fall of 2003, I picked the open pollinated fruit from my single 'KW-8MX' tree and sowed the seed. These grew well the following summer, and in March of 2006, I dug and transplanted 408 seedlings grown from these seeds into a transplant bed. Over the summer of 2006, I inoculated these seedlings with apple scab fungus (*Venturia inaequalis*) and marked all susceptible seedlings for disposal. I also marked for disposal all seedlings with an undesirable visual appearance. Through this selection process, I reduced the 408 seedlings to 59 which were kept for transplanting and further evaluation. The others were destroyed. In the spring of 2007, I transplanted these 59 selected seedlings into a row. These were evaluated for form, foliage, disease resistance, flower quality, and fruit quality over the next three years, and the best 10 trees were selected and transplanted into another row in the same Boring, Oreg. nursery for further selection. In July 2011, it was apparent to me that one single tree out of this group of 10 trees was uniquely superior because of its combination of compact growth, dwarf habit, desirable flowers, clean high quality foliage, and excellent ornamental fruit. I named this tree 'JFS-KW207'. The other 9 selections were destroyed. In January of 2012, I transplanted this original 'JFS-KW207' tree into a long term observation block for further testing and evaluation.

In March of 2012, I took scion wood of 'JFS-KW207' and directed the top grafting onto crabapple stems, grafting 15 trees of which 13 grafts were successful. In March of 2013, I again directed grafting of 15 trees with 14 successful takes. In September of 2013, I directed propagation by budding onto crabapple understock, with 7 of 9 buds being successful. This asexual propagation was accomplished in Canby, Oreg.

Observations of the resulting asexually propagated plants has shown that the characteristics of my new tree are firmly fixed and the asexually propagated trees have been identical to the original tree in every manner that has been observed.

BRIEF SUMMARY OF THE INVENTION

This new cultivar possesses a unique combination of characteristics that have proven firmly fixed in asexually propagated progeny and that comprise a combination of compact growth with dense foliage, a dwarf habit, pink tinted white flowers, brightly colored golden-orange fruit, and clean bright foliage with excellent resistance to the diseases fireblight and scab.

BRIEF DESCRIPTION OF THE DRAWING

The colors of an illustration of this type may vary with lighting conditions and, therefore, color characteristics of this new variety should be determined with reference to the observations described herein, rather than from these illustrations alone. Color descriptions and other terminology are used in accordance with their ordinary dictionary descriptions, unless the context clearly indicates otherwise. The following is a detailed description of my new crabapple tree is made with color descriptions using terminology in accordance with The Royal Horticultural Society (London) Colour Chart©, 1986.

DETAILED BOTANICAL DESCRIPTION

Figure 1:
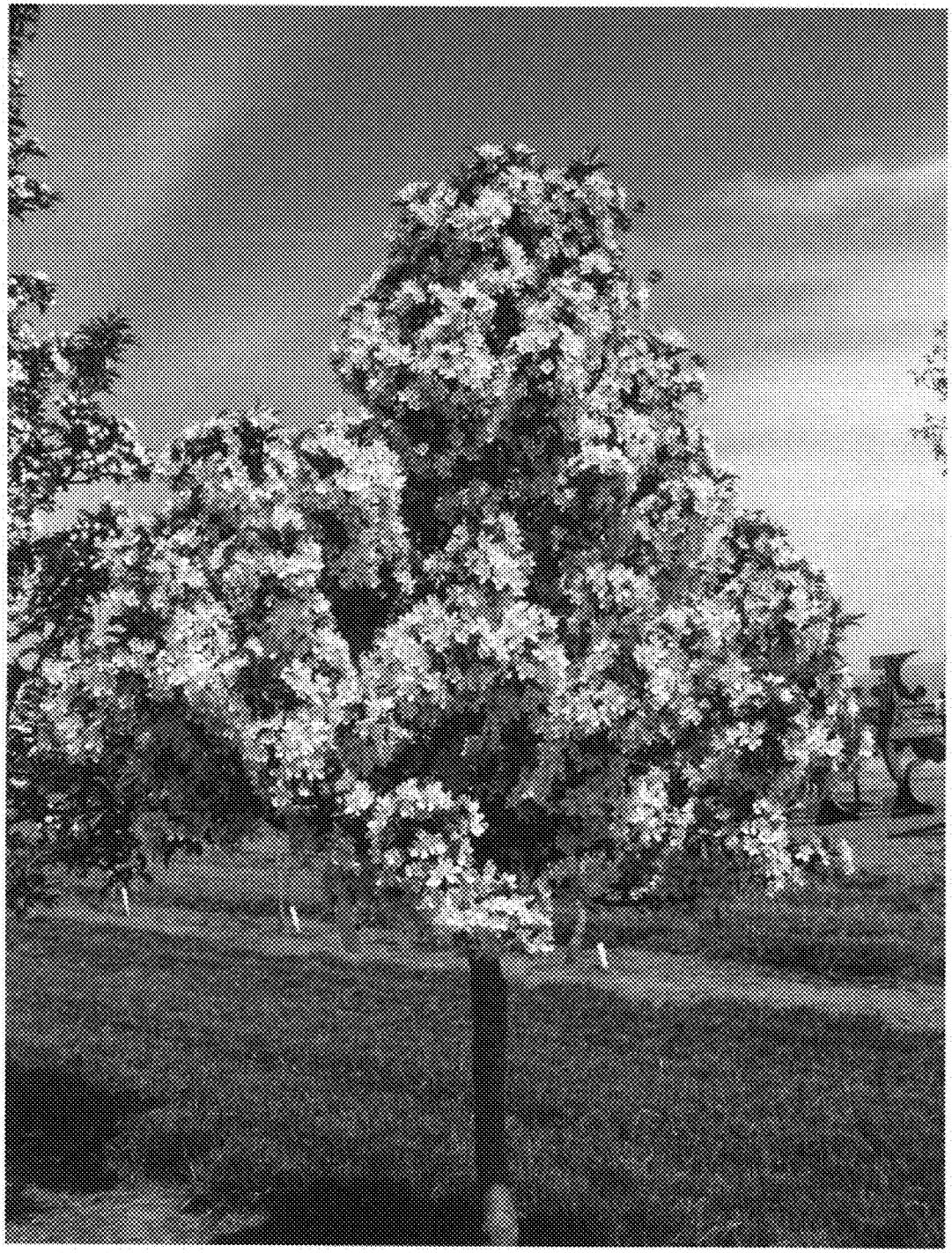
FIG. 1: Shows the original tree in flower at 8 years of age. With its compact, broadly rounded pyramidal to round form and prolific blossoms.
Figure 2:
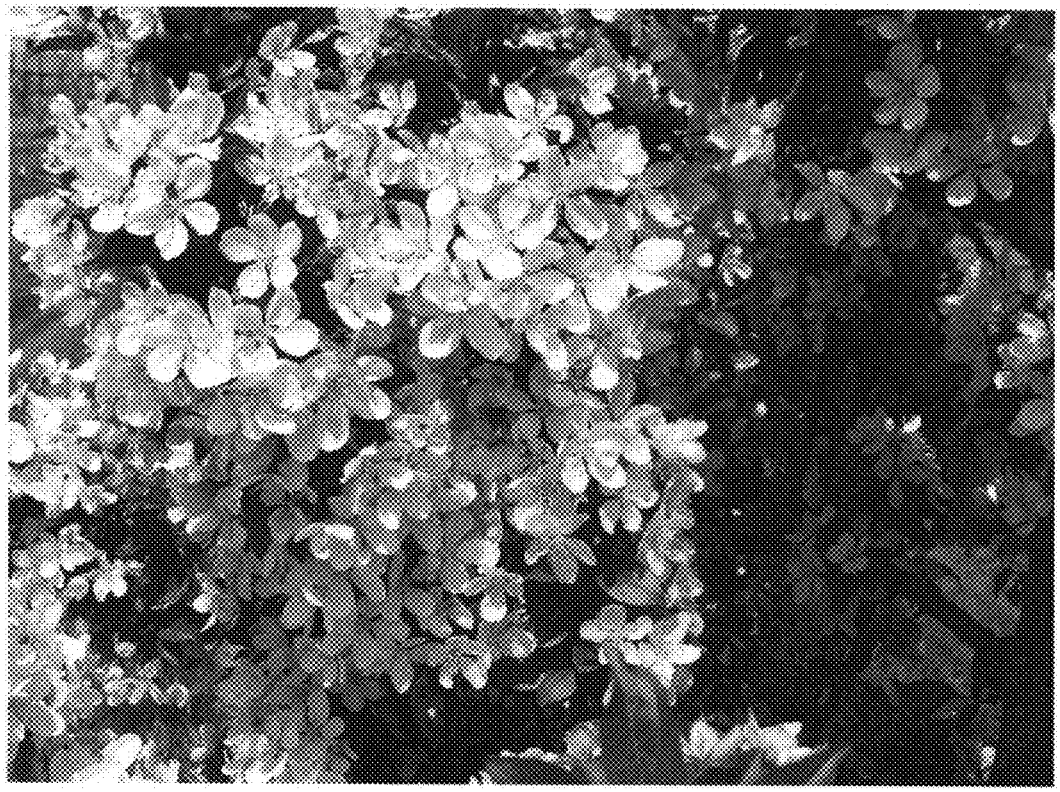
FIG. 2: Shows a close-up of the flowers on the original tree.
Figure 3:
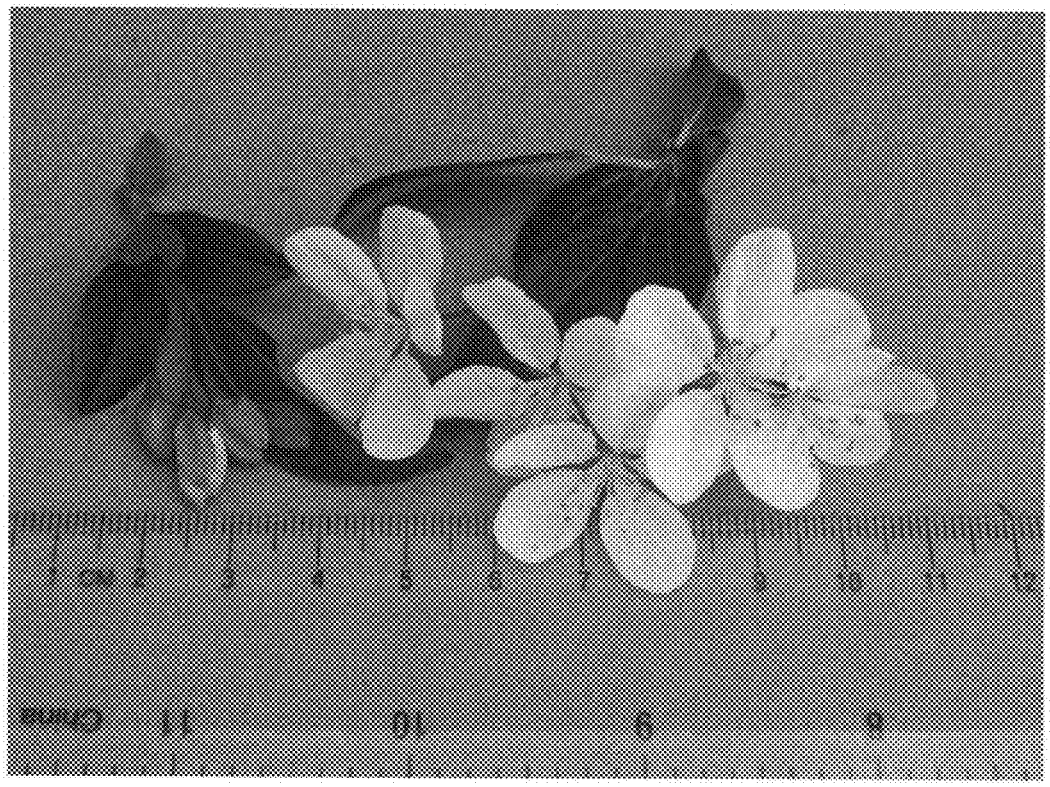
FIG. 3: Shows a close up of a few flowers on a display board with a scale.
Figure 4:
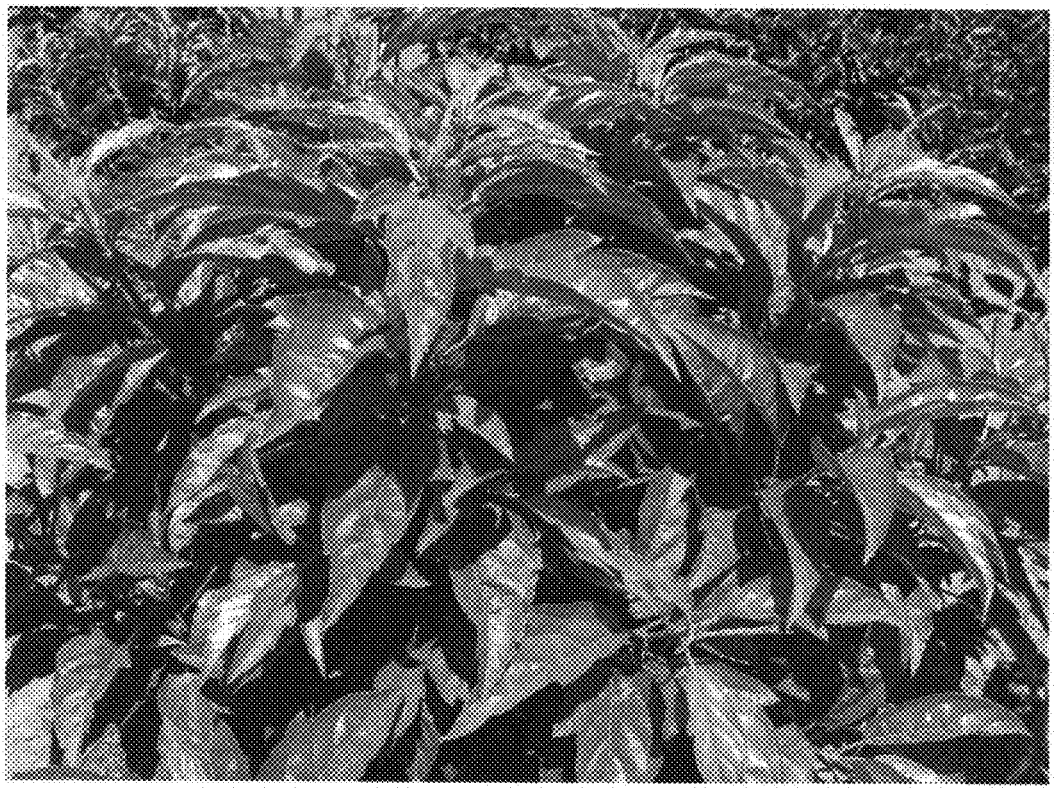
FIG. 4: Shows summer foliage on 2 year vegetatively propagated trees in a nursery row with typical vibrant summer foliage.
Figure 5:
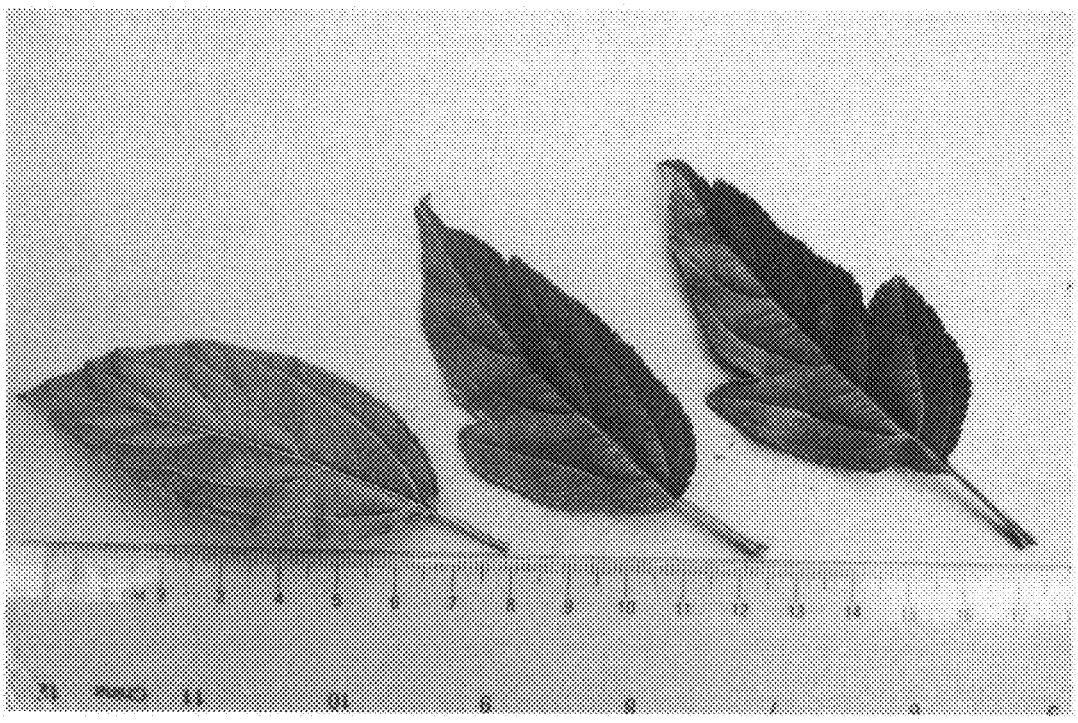
FIG. 5: Shows a close-up of the upper surface of the foliage on a display board with a scale.
Figure 6:
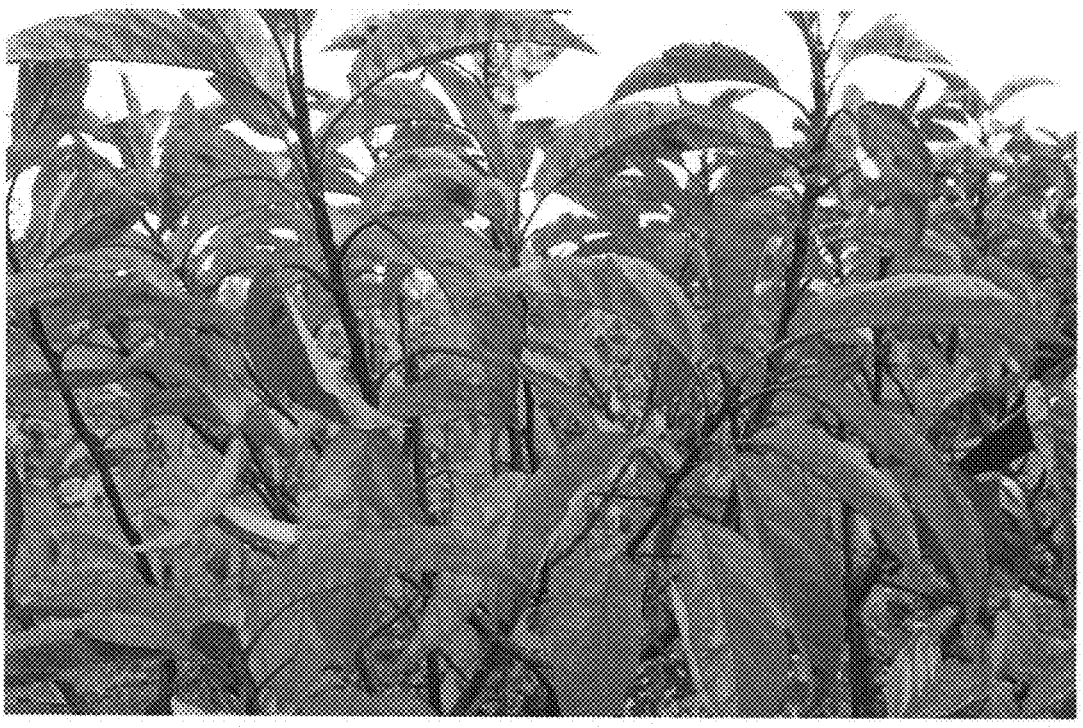
FIG. 6: Shows fall color on 3 year old vegetatively propagated trees in a nursery row.
Figure 7:
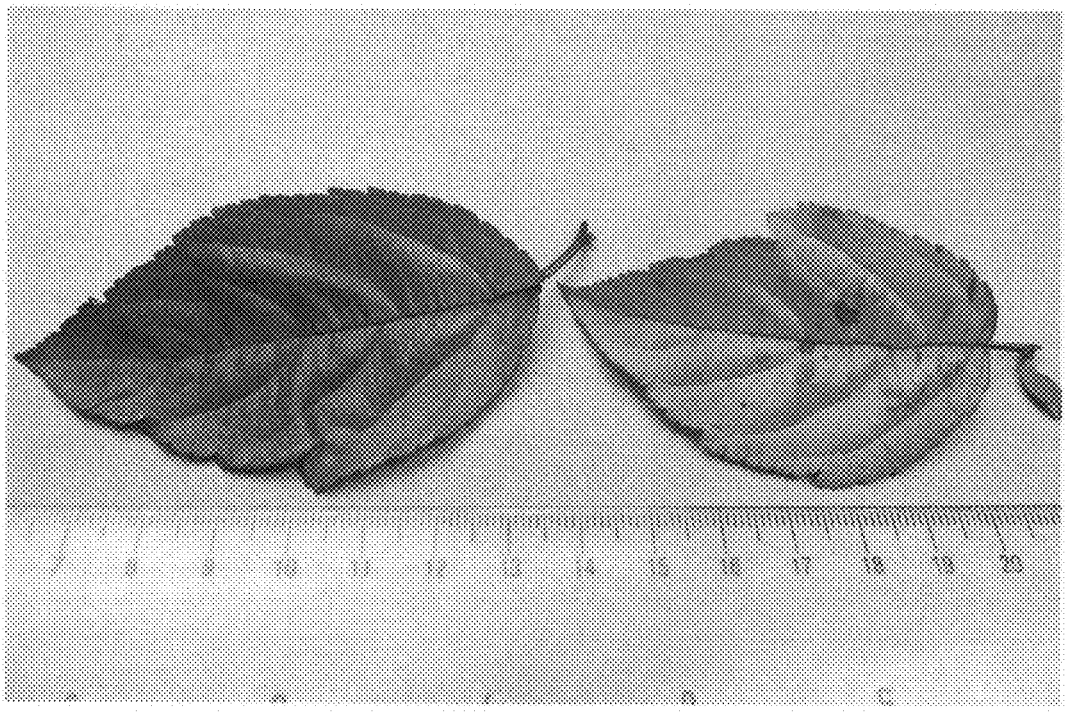
FIG. 7: Shows a close-up of leaves with fall color on a display board.
Figure 8:
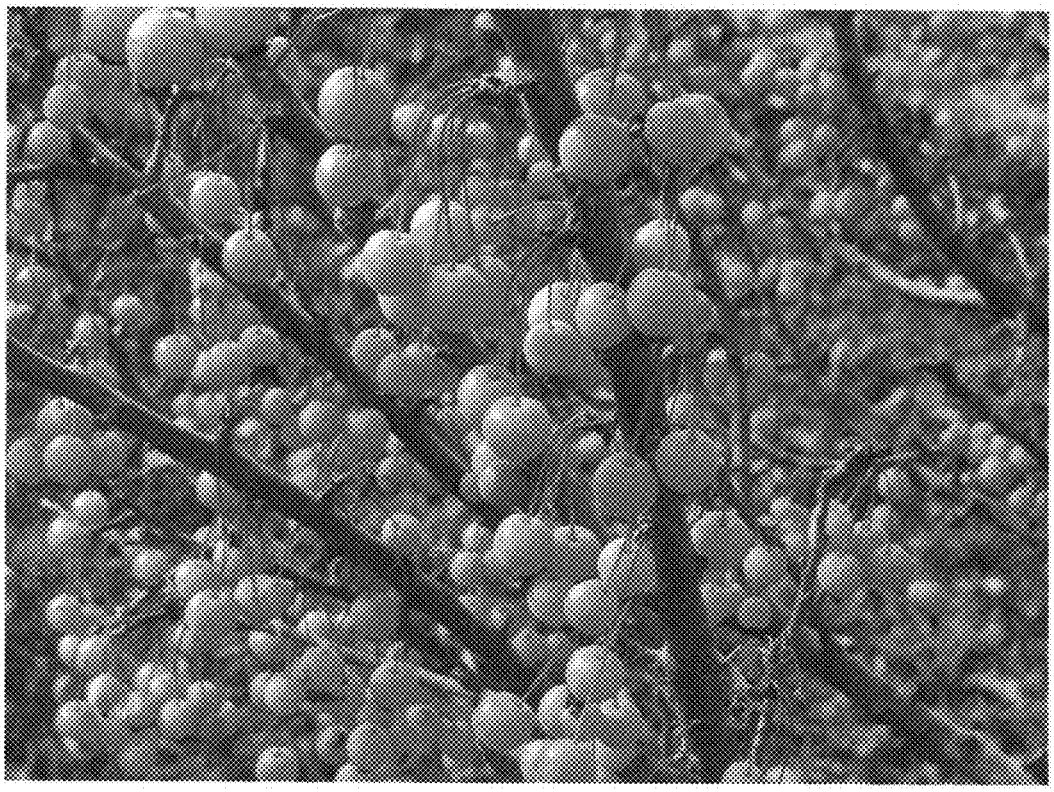
FIG. 8: Shows the original tree with persistent abundant fruit in late November.
Figure 9:
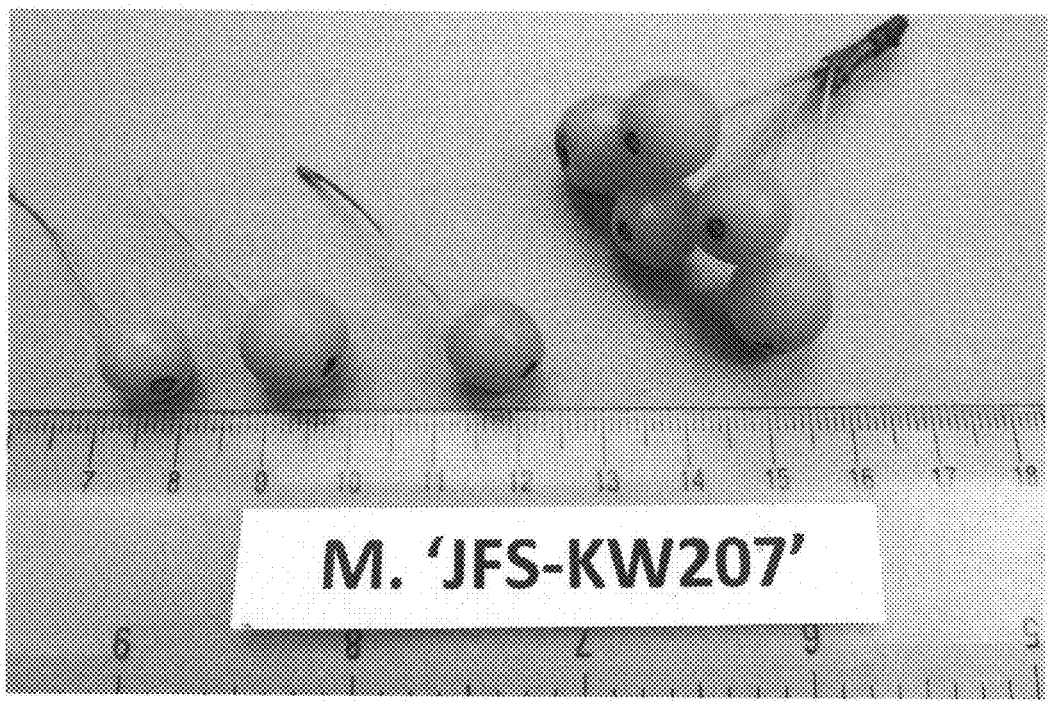
FIG. 9: Shows a close-up of fruit on a display board with a scale.
Figure 10:
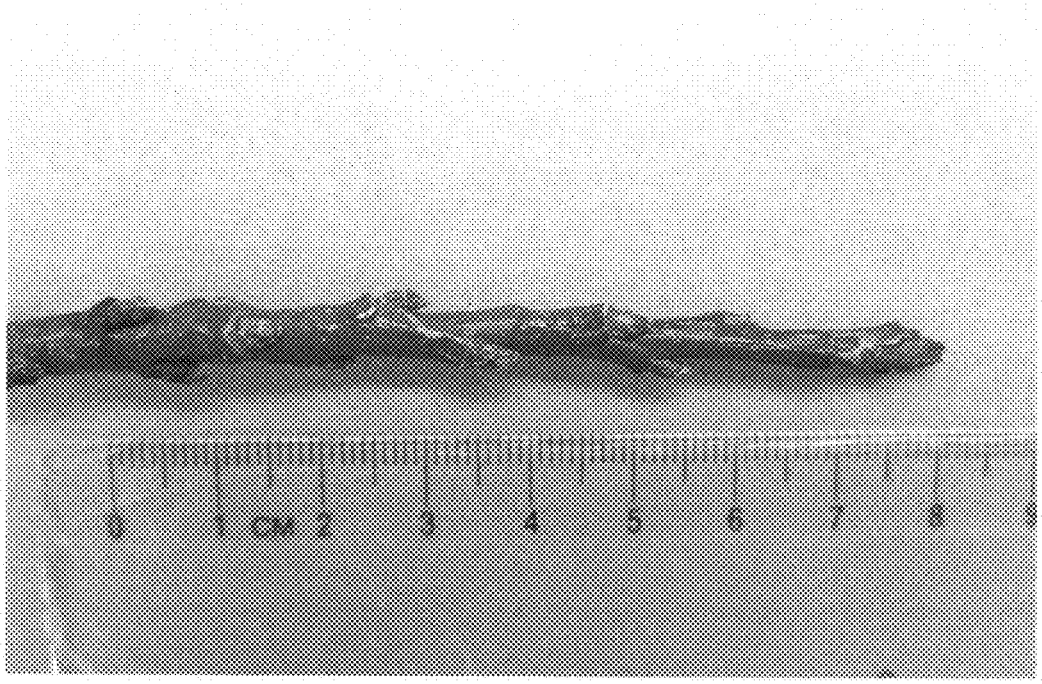
FIG. 10: Shows a dormant branch tip on a display board with a scale illustrating the short internode length.
Figure 11:
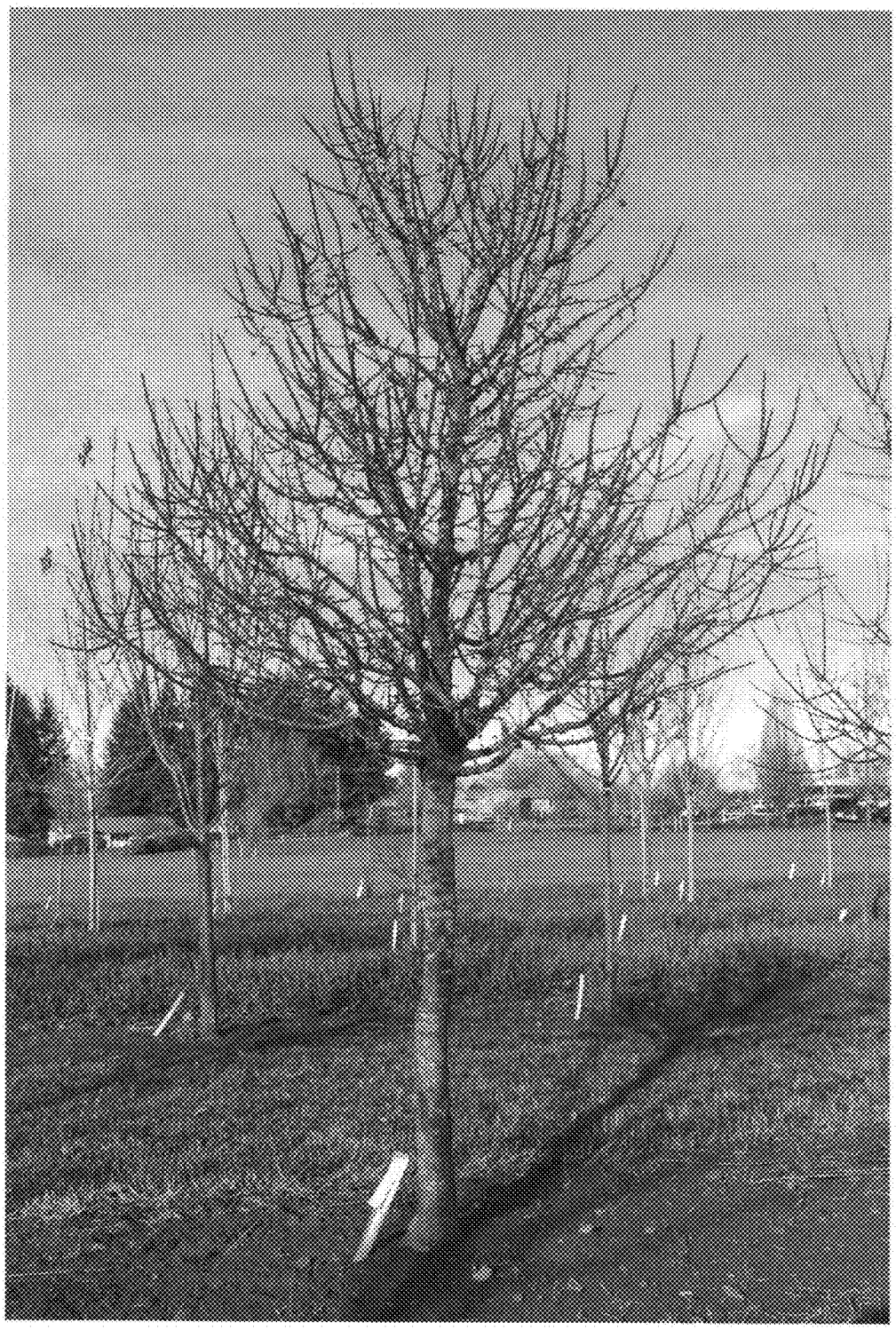
FIG. 11: Shows the original tree without foliage during the winter and illustrating its compact growth habit.

The following detailed description of the 'JFS-KW207' variety is based on observations of the original tree growing in Boring, Oreg. and of two and three year old asexually reproduced 'JFS-KW207' progeny. The observed progeny were trees that were growing in Canby, Oreg.

Scientific name: *Malus* 'JFS-KW207'.

Parentage:

*Seed parent*.—Open pollinated seedling of *Malus* 'KW-8MX' (unpatented).

*Pollen parent*.—Unknown.

Tree:

*Overall shape*.—Compact, broadly rounded pyramidal to round.

*Height*.—Original tree at 8 years of age, about 2.75 meters high.

*Width*.—Original tree at 8 years of age 2.5 meters spread.

*Caliper*.—Original tree at 8 years of age, about 69 mm at 100 mm height, 55 mm at 800 mm height.

*Trunk*.—Strong and straight under nursery growing conditions.

*Trunk bark texture*.—Smooth, vertical fissures with age.

*Trunk bark color*.—Greyed Green 197B to Greyed Green 198A.

*Immature bark color*.—Yellow Green 148A to Greyed Green 197A.

*Mature bark color*.—Greyed Green 197A.

*Trunk lenticels*.—Round to oval 0.25 mm×0.5 mm disappearing by the 3$^{rd}$ year. Orange White 159B in color.

*Primary branches*.—Greyed Green 198A to Grey 201A.

*Branch color*.—Greyed Orange 173A to Greyed Orange 165B.

*Branch lenticels*.—Similar to those on the trunk.

*Dormant buds*.—Oval with acute tip, imbricate scales, 2 mm by 3 mm.

*Internodes*.—Average internode length is about 13 mm on a one-year old shoot.

*Hardiness*.—Has tolerated temperatures to 10 degrees F. in Boring, Oreg. which is the lowest temperature experienced at this location. It is believed to have zone 4 cold hardiness similar to other plants of the same species.

*Disease resistance*.—Excellent resistance to fireblight, powdery mildew & apple scab on foliage and fruit.

Leaves: Except as otherwise noted, observations are from twenty vigorous growth leaves.

*Arrangement*.—Alternate.

*Type*.—Simple, entire, sometimes with 1 to 3 small lobes.

*Texture*.—Smooth, slight undulation between the veins.

*Sheen*.—Slightly glossy.

*Length*.—Averaging 70 mm to 80 mm.

*Width*.—Averaging 30 mm to 40 mm.

*Petioles*.—Averaging 20 mm long, about 1 mm in diameter.

*Overall shape*.—Ovate with 1 or 2 occasional side lobes.

*Margin*.—Serrulate.

*Tip*.—Acute.

*Base*.—Broadly Acute.

*Stipules*.—Two per leaf, 10 mm to 15 mm long by 2 mm to 4 mm wide.

*Summer leaf color*.—Upper leaf surface: Green 139A to Green 137A. Lower leaf surface: Green 138A to Green 139C. Vein: Yellow Green 151B to Yellow Green 145D.

*Fall leaf color*.—Beginning Yellow Orange 23A turning to Orange Red 34B.

*Fall color begins*.—October 30$^{th}$ (Boring, Oreg. 2015).

*Fall color peak*.—November 10$^{th}$ (Boring, Oreg. 2015).

*Fall color ends*.—November 24$^{th}$ (Boring, Oreg. 2015).

*Pubescence*.—None.

*Persistence*.—Tree is deciduous.

Flowers:

*Overall*.—Number of flowers per cluster: 5 to 6.

*Shape*.—Symmetrical, rounded, 5 petals, cupped.

*Size*.—Approximately 25 mm to 30 mm in diameter.

*Unopened bud*.—Red Purple 63A to Red Purple 63C.

*Petals*.—Five petals per flower, 8 mm to 10 mm wide×14 to 16 mm long. Red Purple 63A fading to White 155B. Shape Obovate.

*Sepals*.—Acute, length 1 mm×width 4 mm at base. Red Purple 63A.

*Stamen*.—About fifteen to twenty stamens, 4 mm to 8 mm arranged concentrically around pistil. White 155B.

*Anthers*.—Yellow Orange 16C. 1 to 1.5 mm long by 0.4 mm to 0.5 mm in diameter.

*Pistil*.—Compound, 3 to 5 branched, length about 4 mm-7 mm. Ovary inferior, typically five carpels.

*Pollen*.—Yellow Orange 16C.

*Pedicel*.—28 mm to 38 mm long by 0.4 mm to 0.5 mm in diameter.

*Pubescence*.—None.

*Fragrance*.—Slightly sweet.

*Flowering date*.—In Boring, Oreg. 2015. First bloom March 31$^{st}$, peak bloom April 10th, last bloom April 24th. (Average bloom on all trees in Boring, Oreg. was 2 to 3 weeks early in 2015 compared to typical years).

Fruit: Observations are from a sampling of typical fruit.

*Cluster*.—3 to 4 fruits per cluster.

*Size*.—Typical fruit is 8 mm to 10 mm in diameter by 8 mm to 11 mm long.

*Shape*.—Round to slightly oval.

*Skin*.—Smooth.

*Lenticels*.—None observed.

*Color*.—Immature summer fruit is Yellow Green 144B ripening to yellow 6A in September. Then finally Yellow Orange 21B to Yellow Orange 22A with a blush of Orange 25A on the sun exposed side when fully ripe in October.

*Seeds*.—Typically 3 per fruit, ovoid, about 3 mm long and about 2 mm wide with a smooth surface, Greyed Orange 164B to Greyed Orange 165A in color.

*Fruit production*.—Prolific.

*Fruit persistence*.—95% still persistent November 26$^{th}$ (2014 and 2015). Usage: Ornamental, non-edible.

COMPARISON TO THE SEED PARENT

Compared to the seed parent tree 'KW-8MX', my new cultivar 'JFS-KW207' has a denser, more rounded habit, larger flowers with a better shape, better resistance to apple scab, and more persistent fruit. 'KW-8MX' has a slightly open dwarf form which develops into the shape of an inverted cone while 'JFS-KW207' is tightly compact, dense, and broadly rounded pyramidal to round. 'KW-8MX' flowers are 25% smaller and have petals with a wavy margin and a somewhat distorted appearance while 'JFS-KW207' flowers are round and have petals with a smooth margin. 'KW-8MX' is moderately scab resistant while 'JFS-KW207' is highly scab resistant. Finally, 'KW-8MX' has fruit that is only moderately persistent in the fall and completely drops from the tree by November 30$^{th}$ under typical Boring, Oreg. conditions while the majority of fruit of 'JFS-KW207' holds on the tree into mid-December.

COMPARISON TO OTHER SIMILAR VARIETIES

| | 'JFS-KW207' | 'Coralcole' (unpatented) | 'Lollizam' (unpatented) |
|---|---|---|---|
| Leaf Length | 70 mm to 80 mm | 50 mm to 55 mm | 60 mm to 75 mm |
| Leaf Width | 30 mm to 40 mm | 14 mm to 16 mm | 30 mm to 35 mm |
| Petiole | 20 mm | 15 mm | 15 mm to 20 mm |
| Upper Leaf Color | Green 137A to Green 139A | Green 133A to Green 135A | Green 133A to Green 132B |
| Pubescence | None | Yes, slight | Yes, Slight |
| Branch Color | Greyed Orange 165B to Greyed Orange 173A | Greyed Purple 187A | Greyed Purple 183B to Greyed Purple 187C |
| Fruit Color (mature) | Yellow Orange 21B to Yellow Orange 22A | Yellow 8A to 10A | Red 44B to Red 46B |
| Fruit Size | 8 to 10 mm to 8-11 mm | 8 to 10 mm to 8 to 9 mm | 7 to 8 mm to 9 to 12 mm |
| Fruit Shape | Round | Round | Ovoid |

I claim:

1. A new and distinct variety of crabapple tree, substantially as herein illustrated and described.

* * * * *